United States Patent
Ureche et al.

[11] Patent Number: 5,431,664
[45] Date of Patent: Jul. 11, 1995

[54] METHOD OF TUNING ULTRASONIC DEVICES

[75] Inventors: Alexander Ureche, Mission Viejo; Kurt D. Leukanech, Aliso Viejo, both of Calif.

[73] Assignee: Alcon Laboratories, Inc., Fort Worth, Tex.

[21] Appl. No.: 234,765

[22] Filed: Apr. 28, 1994

[51] Int. Cl.⁶ .................. A61B 17/00; A61F 9/00
[52] U.S. Cl. ........................... 606/128; 606/169; 606/171; 604/22; 331/154; 310/316
[58] Field of Search .................. 310/314–318; 601/2; 604/22; 606/169–171; 331/154

[56] References Cited

U.S. PATENT DOCUMENTS

| | | |
|---|---|---|
| 3,964,487 | 6/1976 | Judson . |
| 4,126,137 | 11/1978 | Archibald . |
| 4,180,074 | 12/1979 | Murry et al. . |
| 4,428,748 | 1/1984 | Peyman et al. . |
| 4,642,581 | 2/1987 | Erickson ............... 331/154 |
| 4,808,948 | 2/1989 | Patel et al. ............ 331/154 |
| 4,933,843 | 6/1990 | Scheller et al. . |
| 4,973,876 | 11/1990 | Roberts ............... 310/316 |
| 5,139,509 | 8/1992 | Fischer et al. . |
| 5,160,317 | 11/1992 | Costin . |
| 5,279,547 | 1/1994 | Costin . |
| 5,331,951 | 7/1994 | Kepley . |
| 5,370,602 | 12/1994 | Kepley . |

FOREIGN PATENT DOCUMENTS

| | | |
|---|---|---|
| 0424686A1 | 5/1991 | European Pat. Off. . |
| 0586882A1 | 3/1994 | European Pat. Off. . |

*Primary Examiner*—Krista M. Zele
*Attorney, Agent, or Firm*—Jeffrey S. Schira

[57] ABSTRACT

A method of tuning ultrasonic transducers by using the admittance of the transducer as the tuning parameter rather than the phase angle. The admittance magnitude of a transducer is not related to the phase angle and thus, using the admittance of the transducer as the tuning parameter allows tuning over a broad bandwidth. In addition, transducer performance can be normalized against the variation in admittance magnitude and frequency location of the series and parallel resonance points by quantifying these variations and continually adjusting the operational set point as a function of transducer drive voltage during transducer operation.

15 Claims, 8 Drawing Sheets

FIG. 8

METHOD OF TUNING ULTRASONIC DEVICES

BACKGROUND OF THE INVENTION

The present invention relates to a method of tuning ultrasonic devices and more particularly to a method for tuning ophthalmic phacoemulsification handpieces.

A typical ultrasonic surgical device suitable for ophthalmic procedures consists of an ultrasonically driven handpiece, an attached cutting tip, an irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363, 4,223,676, 4,246,902, 4,493,694, 4,515,583, 4,589,415, 4,609,368, 4,869,715 and 4,922,902, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

The horn (transducer) assembly, including both piezoelectric and high endurance limit inert materials, used in ultrasonic handpieces must be carefully tuned for proper operation. As used herein, "tuning" is the process of finding and tracking the correct resonant frequency of the handpiece operating under loaded or unloaded conditions. Operating the handpiece at resonance takes advantage of the transducer's energy storage capabilities, which occurs only at resonance. With proper tuning, the transducer will store mechanical energy while operating unloaded and release this energy into the material being cut when loaded. As a consequence, for short periods of time, large amounts of energy can be directed into the material by the transducer itself and not by the transducer's power source. This allows the power source to be designed to handle only the steadystate power requirement of the transducer and not the loaded transients which can be many times higher.

Prior to the present invention, the usual way of determining the resonant frequency of a transducer was to compare the phase angle between the voltage applied to the transducer and the current drawn by the transducer. When alternating voltage is applied to a circuit, current will flow through the circuit. The amount of current is determined by dividing the voltage by the impedance of the circuit according to Ohm's Law. If the circuit is purely resistive, the impedance is equal to the total resistance in the circuit and the current equals the voltage divided by the circuit resistance.

When the voltage and current waveforms are viewed on an oscilloscope for a particular circuit, if the circuit is inductive, current will lag voltage and, if the circuit is capacitive, the voltage will lag the current. The time difference between the points when the voltage and current waveforms intersect the zero axis is measured in trigonometric terms by the phase angle $\phi$. For purely resistive circuits, $\phi=0$ and the voltage and the current are said to be in phase. For purely inductive circuits, $\phi=90°$ and for purely capacitive circuits, $\phi=-90°$ and the voltage and the current are said to be out of phase.

For circuits containing all three elements, resistors, inductors and capacitors, there will be some frequencies where the total impedance of the circuit will appear purely resistive even though the circuit contains reactive elements. These frequencies are the resonant frequencies. Consequently, one method of determining the resonant frequencies of a complex circuit is to apply an alternating voltage to the circuit and vary the frequency until the phase angle $\phi$ between the voltage and current is zero. The frequencies where this condition occurs are the resonant frequencies. As discussed above, when driving a circuit having both resistive and reactive components, it is important to know the value of the phase angle $\phi$ because the power absorbed by the circuit is directly proportional to the cosine of the phase angle ($\cos(\phi)$). For a phase angle equal to zero, $\cos(0)=1$ (unity) and the transfer of power from the source to the circuit is at a maximum, this is the case for purely resistive loads. However, if $\phi=90°$ or if $\phi=-90°$, as is the case for reactive loads, the $\cos(\phi)=0$ so there is no power transferred through the circuit. $\cos(\phi)$ is referred to as the power factor.

Ultrasonic devices driven by piezoelectric or magnorestrictive elements present complex equivalent circuits that are a combination of capacitors, inductors and resistors and generally have more than one resonant frequency. In fact, for these electromechanical transducers, the resonant frequencies occur in pairs of closely spaced frequencies where the impedance is resistive and the phase angle $\phi$ is zero. One of these resonant frequencies is called the series resonant frequency and the other resonant frequencies is called the parallel resonant frequency or the antiresonance. When the ultrasonic device is driven at either of these frequencies the power factor is equal to unity and the transfer of power is maximized.

However, the phase angle of the ultrasonic device is dependent on the amount of loading on the transducer. This loading is generally understood to mean resistive-type loading that will have a damping effect on the vibrations of the transducer. The series and parallel resonant frequencies exist only if the transducer is unloaded or only lightly loaded. If the resistive loading on the transducer is increased above a threshold amount, the transducer will no longer resonate because the load totally dampens the vibrations of the transducer. When this condition occurs, $\phi$ will no longer be zero and the transfer of power will no longer be optimum. The addition of a tuning inductor in series with the transducer will produce a resonant and, consequently, a zero phase angle condition no matter how heavy the load. This inductor, however, adds a third resonant frequency to the circuit when the device is operated under a no load or small load condition. This third frequency must be differentiated from the series and parallel resonant frequencies during tuning.

Figure 6:
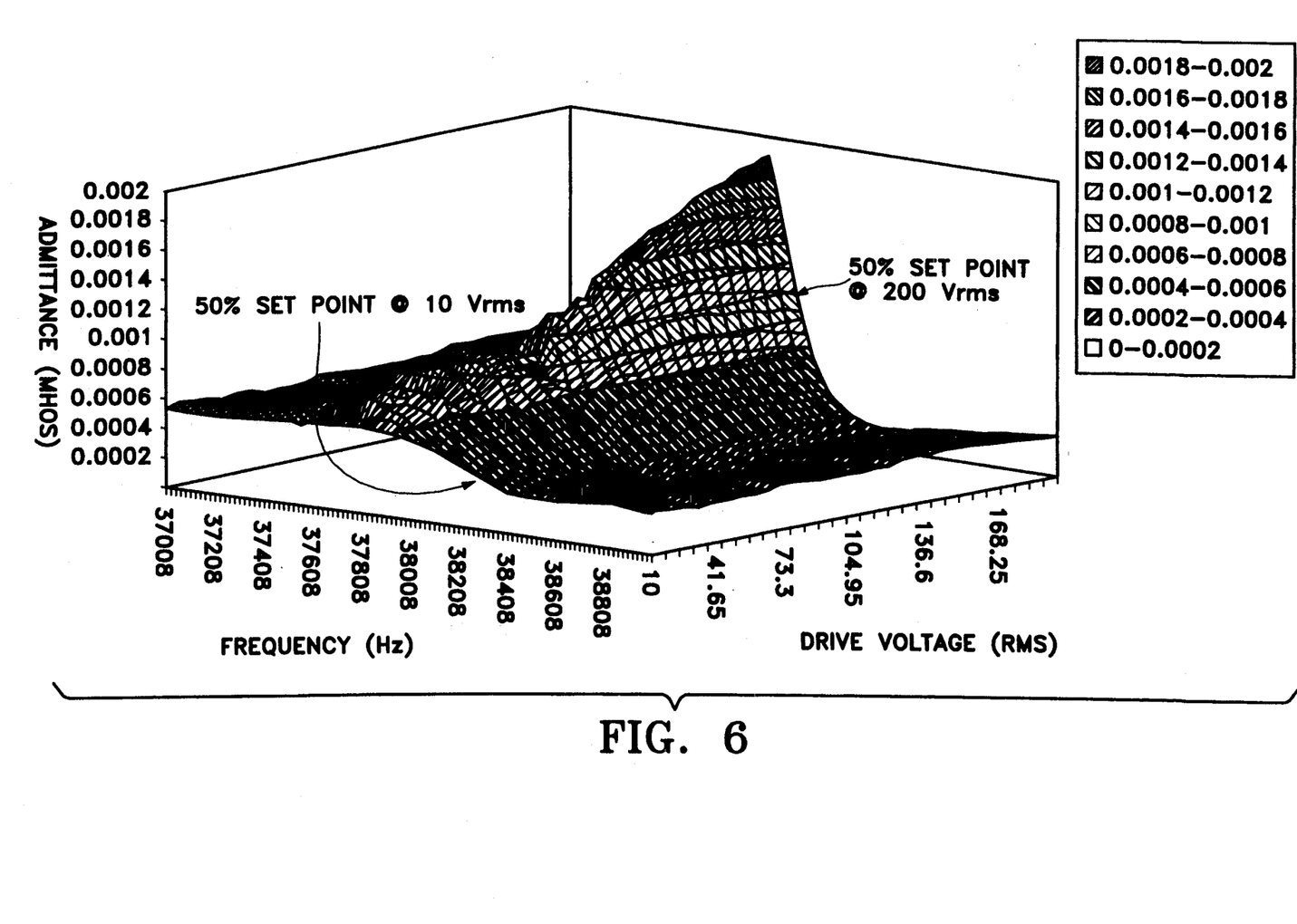
FIG. 6 is a three dimensional graph plotting admittance versus frequency versus drive voltage for a typical piezo electric ultrasonic transducer operating immersed in a water bath.
Figure 7:
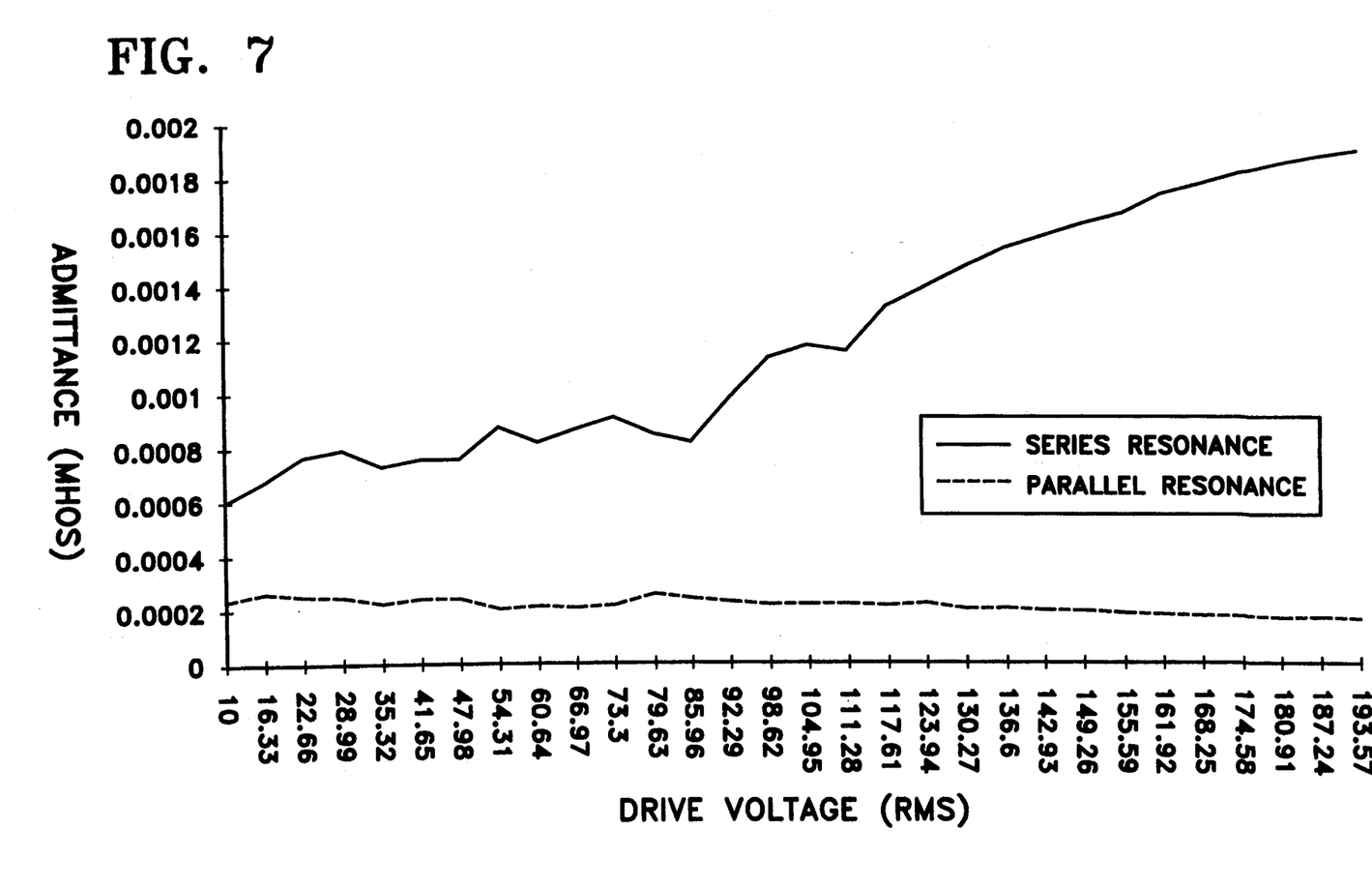
FIG. 7 is a graph of the variation in admittance magnitude of the series and parallel resonance points as a function of drive voltage for the same data depicted in FIG. 6.
Figure 8:
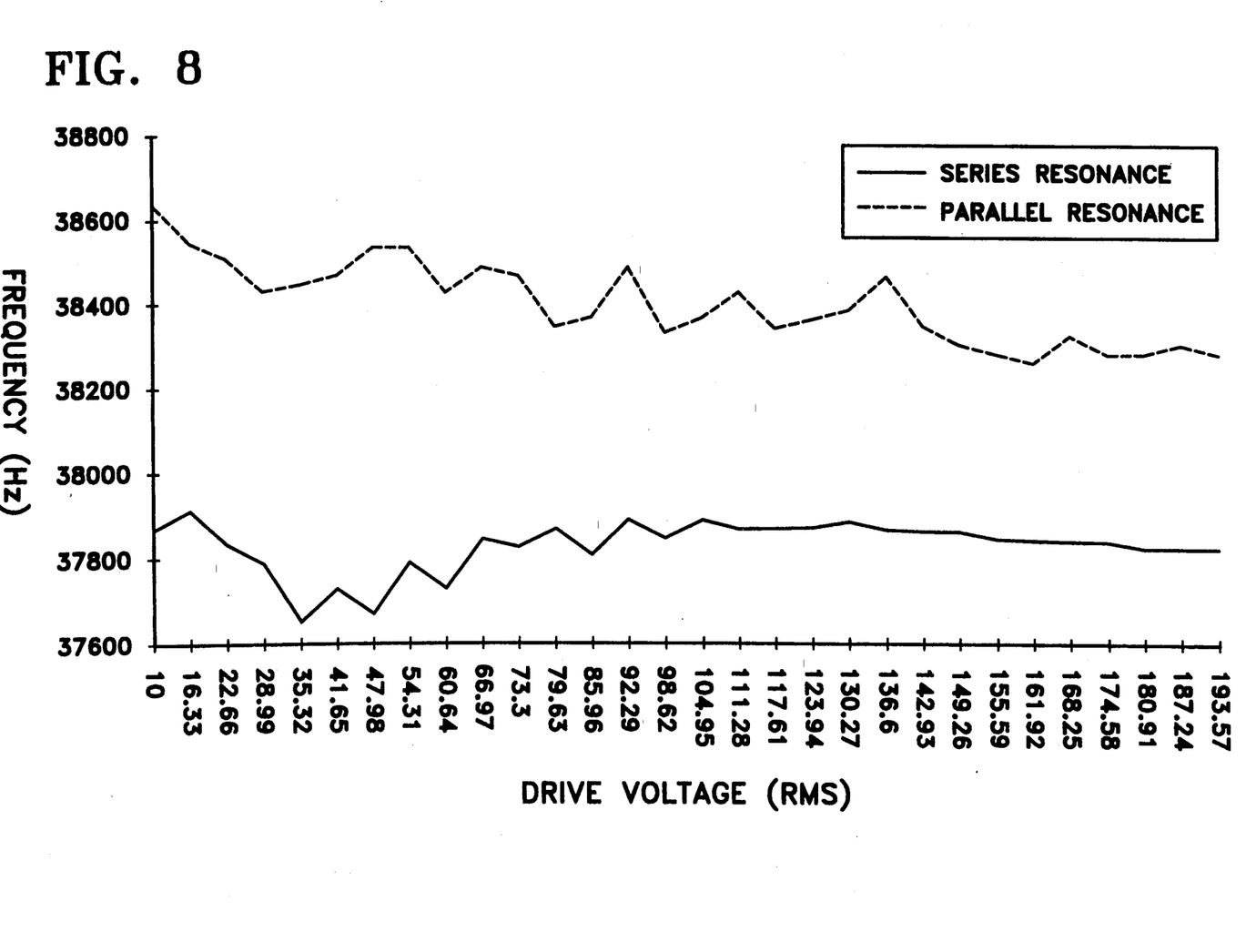
FIG. 8 is a graph of the series and parallel resonance points as a function of voltage for the same data depicted in FIG. 6.

Prior art tuning methods generally use phase locked looped circuits with very narrow tuning ranges centered around one of the resonant frequencies discussed above. While this approach is suitable for drivers used in combination with transducers having operating resonances very close to each other, this approach is unsuitable for drivers used in combination with transducers with resonant frequencies that are considerably far apart. The prior art "one dimensional" tuning methods also limit transducer performance over a wide dynamic range of drive voltages because the series and parallel resonance frequencies and admittance will vary with drive voltage, as shown in FIGS. 6, 7 and 8. FIG. 6 illustrates a three dimensional view of an actual transducer admittance magnitude as a function of frequency and drive voltage, and illustrates the obvious change in the shape of the transducer characteristics as a function of voltage and frequency. FIG. 7 illustrates the variation in admittance magnitude of the series and parallel resonance points as a function of drive voltage for the same data used to generate FIG. 6. FIG. 8 illustrates the shift in the frequency location of the series and parallel resonance points as a function of voltage for the same data used to generate FIG. 6.

Accordingly, a need continues to exist for a method tuning ultrasonic devices operating at greatly varying resonant frequencies and drive voltages.

BRIEF DESCRIPTION OF THE INVENTION

The present invention improves upon prior art methods of tuning ultrasonic devices by using the admittance of the transducer as the tuning parameter rather than the phase angle. The admittance magnitude of a transducer is not related to the phase angle and thus, using the admittance of the transducer as the tuning parameter allows tuning over a broad bandwidth, for example 20 kilohertz (khz) to 100 khz. In addition, the present invention normalizes transducer performance against the variation in admittance magnitude and frequency location of the series and parallel resonance points by quantifying these variations and continually adjusting the operational set point frequency as a function of transducer drive voltage during transducer operation. This "multi-dimensional" tuning method yields a significant improvement in transducer performance over a widely varying transducer output range. The improved transducer performance results in a transducer output (stroke) over a wider dynamic range, increased transducer output linearity, more consistent transducer output over time and more consistent performance between different transducers operating on the same control console.

Accordingly, one objective of the method of the present invention is to allow tuning of ultrasonic devices over a broad bandwidth.

Another objective of the method of the present invention is to allow tuning of ultrasonic devices operating at greatly varying resonant frequencies.

Still another objective of the method of the present invention is to improve performance of ultrasonic devices operating at varying drive voltages.

Still another objective of the method of the present invention is to provide a tuning method for ultrasonic devices that is not dependent on phase angle.

These and other objectives and advantages of the present invention will become apparent from the drawings, detailed description and claims which follow.

DETAILED DESCRIPTION OF THE INVENTION

The inventors have discovered that for ultrasonic devices operating under fairly constant resistive loads, the admittance of the device can be used as the tuning parameter and, because the admittance is not dependent on phase angle, using the admittance as the tuning parameter allows the tuning method to operate over a broad bandwidth. Admittance is generally defined as the reciprocal of the impedance (i.e. the ratio of current to voltage). To determine the admittance, both the current and the voltage must be measured in the same units, for example, RMS values as measured by a typical volt meter. Either peak to peak or average values for current and voltage may be used. In both cases, the measured admittance is generally referred to as the modulus or the magnitude of the admittance.

Figure 2:
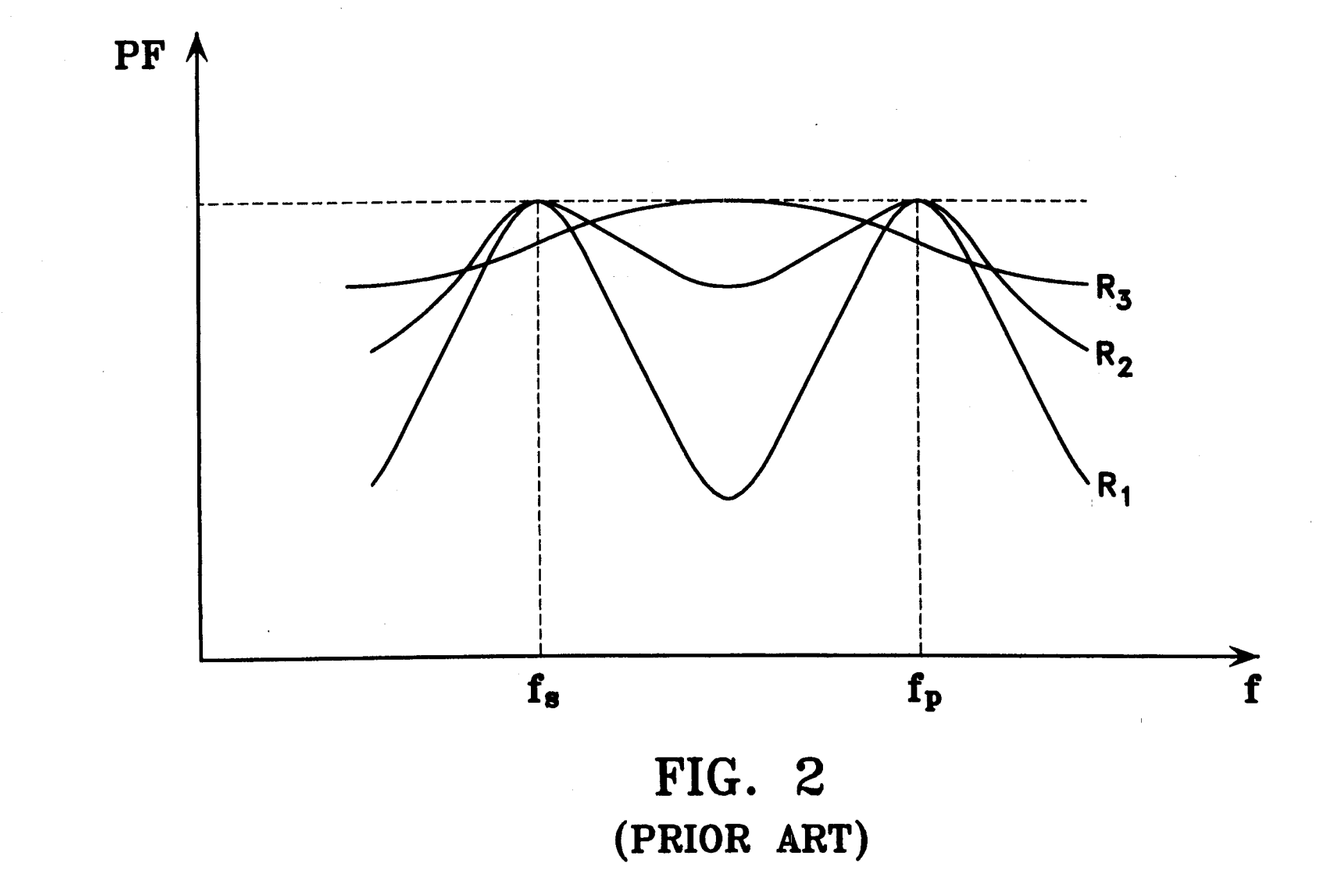
FIG. 2 is a graph plotting power factor versus the frequency for a typical ultrasonic device under three different resistive loading conditions.

An unloaded transducer with a very low loss resistance will draw power from the source only at either the series ($f_s$) or the parallel ($f_p$) resonant frequencies where the power factor is very close to unity. Between these two frequencies and outside this frequency range the power factor drops to near zero and little power is drawn from the source. For a resistively loaded transducer, however, the power factor will be different from zero even for frequencies between the series and parallel frequencies. By "resistive" loads, what is meant are loads that produce damping effects on the transducer, usually though friction. Water, bodily fluids, and viscous or soft materials generally are resistive loads. As illustrated in FIG. 2, for typical piezoelectric transducers used in medical surgical applications where the irrigation/aspiration fluid represents a permanent resistive load and operating at a power level below 100 watts, the power factor will not always be unity but usually is greater that 0.5. However, as the load increases, the frequency difference between the series and parallel resonant frequencies decreases until at some "critical" resistive load level ($R_3$), the series and parallel resonant frequencies are equal and the power factor is unity. This condition generally occurs at a frequency equal to the midpoint between the series and parallel resonant frequencies. The electrical value of this critical load is equal to the reactance of the electrical capacitance of the piezoelectric element of the transducer. At loads above $R_3$, the transducer will not resonate.

Figure 1:
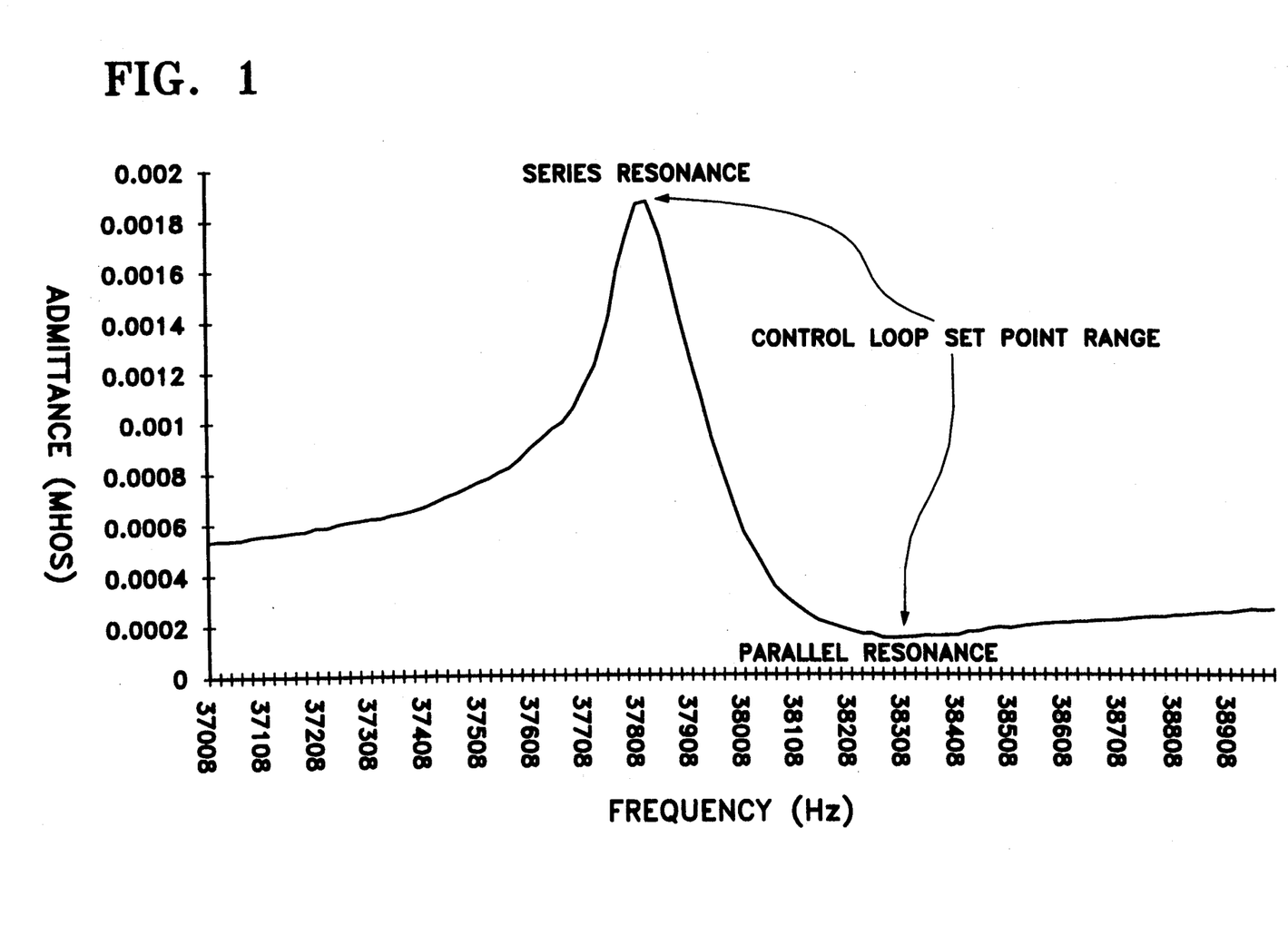
FIG. 1 is a graph plotting admittance versus frequency for a typical ultrasonic device.

As illustrated in FIG. 1, the typical admittance for a piezoelectric transducer is at a maximum at the series resonant frequency and at a minimum at the parallel resonant frequency. For frequencies lower or higher than the series and parallel resonant frequencies, the admittance curve is essentially a straight line because, when out of the tuning range, the transducer experiences little motion. Thus, the mechanical effects are negligible and the input impedance of the transducer is essentially equal to the electrical capacitance of the piezoelectric crystal and because admittance is directly proportional to frequency ($Y = \omega^* C$), when the admittance is plotted as a function of frequency, the graph is a straight line. By scanning the admittance of a transducer over a given frequency range, both the series and parallel resonant frequencies are easily determined because the series resonant frequencies coincides with the maximum admittance and the parallel frequency coincides with the minimum admittance.

Figure 3:
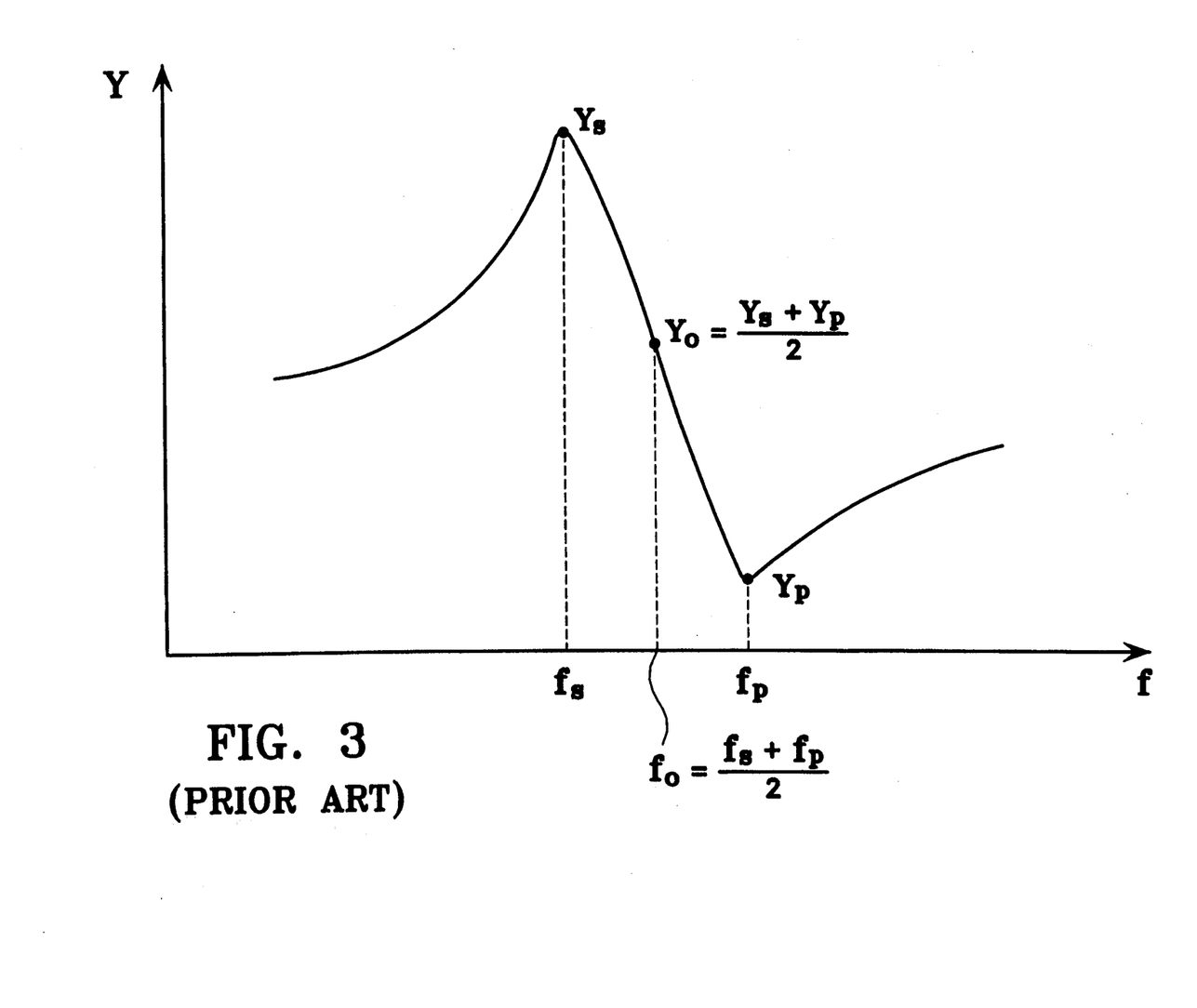
FIG. 3 is a graph similar to the graph illustrated in FIG. 1 and illustrating the middle point admittance for a typical ultrasonic device.
Figure 4:
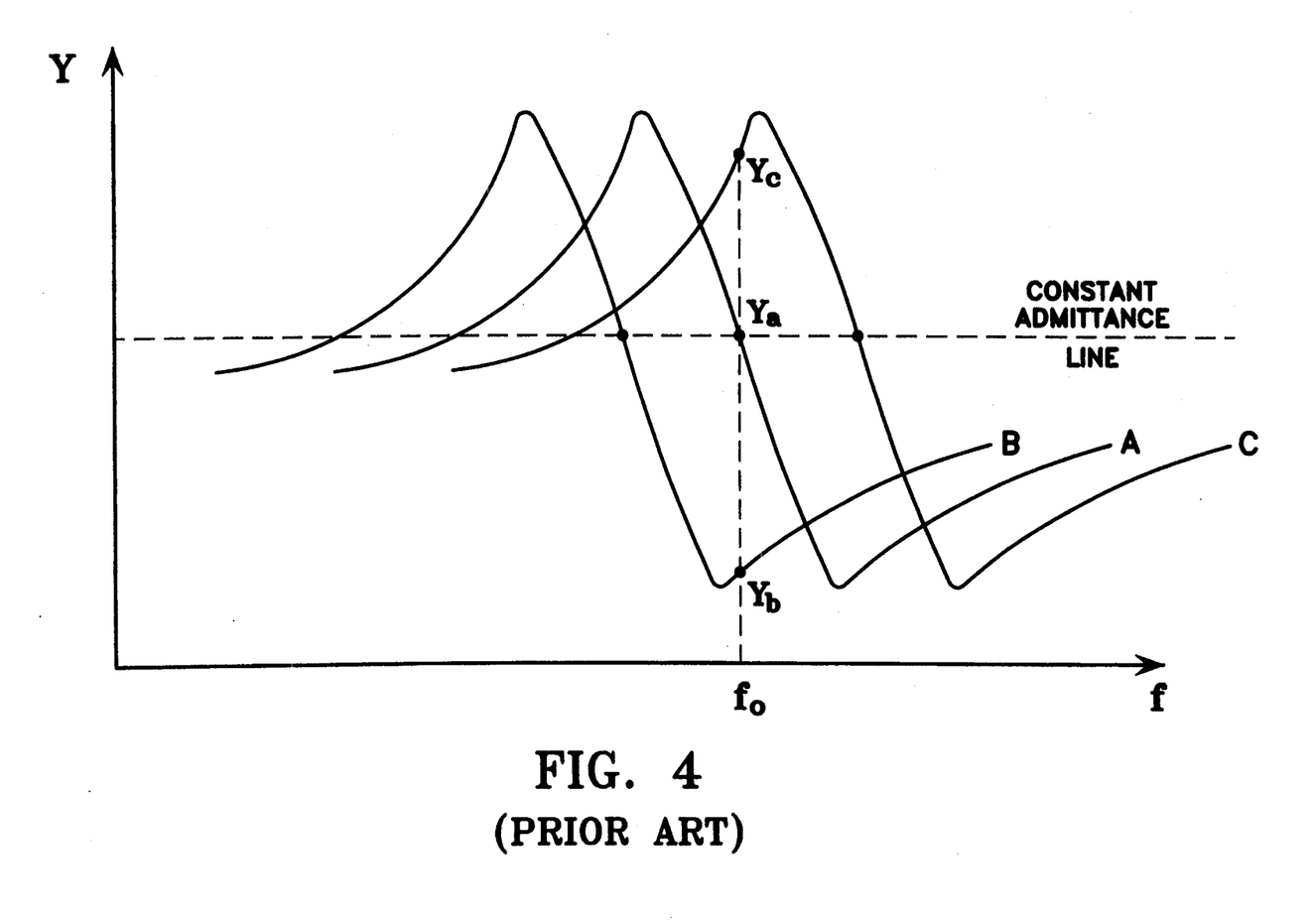
FIG. 4 is a graph similar to the graphs illustrated in FIGS. 1 and 3 and illustrating the frequency shift that occurs under reactive loading for a typical ultrasonic device.
Figure 5:
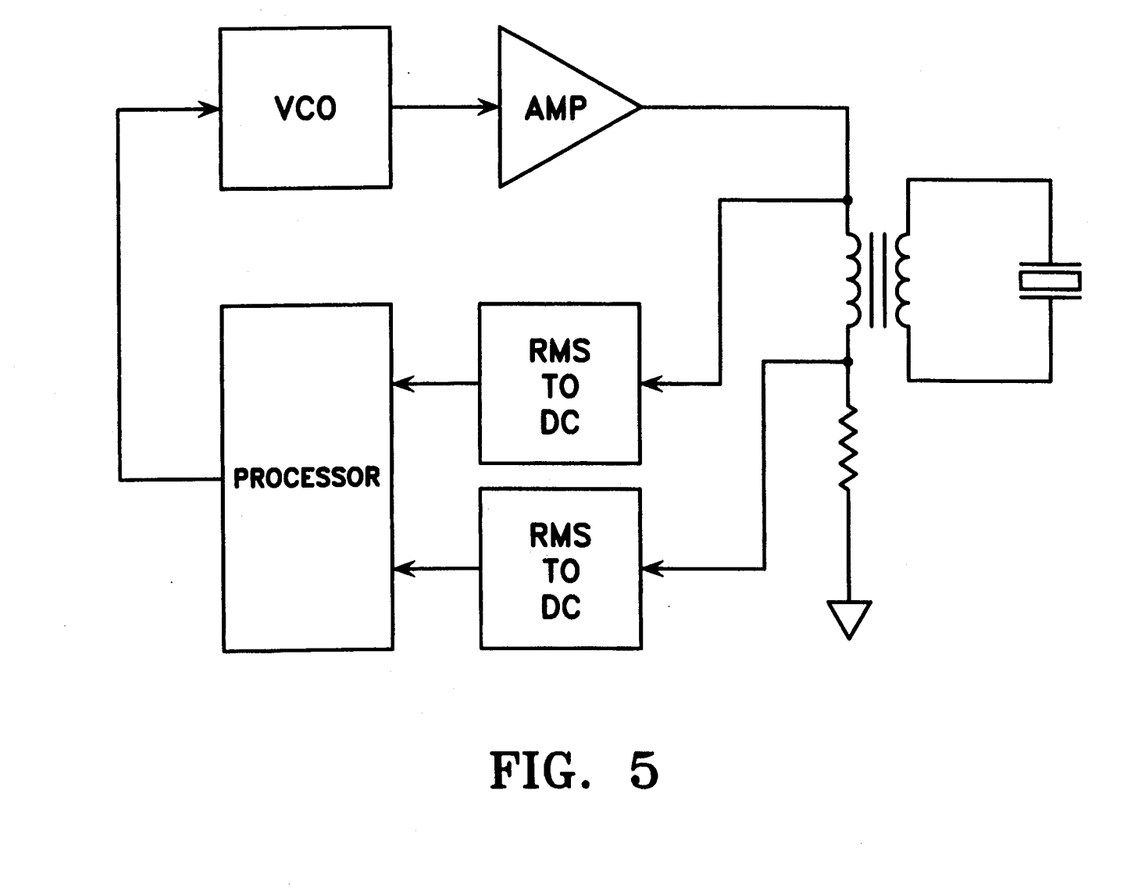
FIG. 5 is a block diagram of one apparatus suitable for implementing the present invention

While the above discussion is limited to resistively loaded transducers, by using the admittance of the transducer as the tuning parameter, frequency tracking for reactive loads is facilitated. Reactive loads either add mass or add compliance to the transducer. These reactive loads either increase or decrease the operational frequency of a transducer. As illustrated in FIG. 4, line A illustrates the admittance curve for an unloaded or purely resistively loaded transducer. The addition of a mass reactive load decreases the operational frequency of the transducer and causes the entire admittance curve to shift to the left along the frequency line as illustrated by line B. Similarly, the addition of a compliant reactive load increases the operational frequency of the transducer and causes the entire admittance curve to shift to the right along the frequency line as illustrated by line C. While there is no shift in the Y direction (no increase in the magnitude of the admittance) with the addition of a reactive load, the shift in the admittance curve will cause the admittance to vary along with the frequency except at the frequency ($f_o$) occurring at the midpoint between the series and parallel resonant frequencies ($f_s/2 + f_p/2$, see FIG. 3). The admittance at this midpoint frequency $f_o$ will remain constant despite any reactive shifts in the admittance curve. Therefore, using the admittance at frequency $f_o$ allows for tuning of a transducer over a broad bandwidth. While $f_o$ can be determined arithmetically, $f_o$ can also be determined by using the following equation:

$$f_o = (f_s * \alpha) + (f_p * (1 - \alpha))$$

where $0 < \alpha < 1$.

In use, the admittance of a transducer is measured over a given frequency range and $f_s$ and $f_p$ are determined in the manner described above. Once $f_s$ and $f_p$ are determined, $f_o$ is easily calculated and the admittance for this frequency is already known. By either increasing or decreasing the operational frequency Of the transducer so that the admittance stays constant at this value will result in uniform tuning of the transducer.

The present invention also contemplates tuning the operational set point of the transducer as a function of drive voltage. Any of the various operating parameters (admittance, phase, impedance, current, power and voltage, either alone or in combination) of the transducer can be measured over a relatively wide range at two or more drive voltage levels. By correlating the drive voltage and frequency to the magnitude of the particular parameter examined, the operation of the transducer can be controlled by varying frequency.

For example, the admittance of a transducer can be measured by sweeping the operational frequency in the manner discussed above over two or more drive voltages. For optimum transducer performance, an admittance value is selected intermediate of the series and parallel resonance frequencies. This admittance value is used as the operational set point admittance. By determining the operational set point admittance in this way over many different voltage levels, an equation for the operational set point as a function of drive voltage can be determined by linear regression analysis. With this method, the operational set point value of the transducer for any drive voltage can be maintained by varying the frequency of the transducer, thereby allowing for more consistent performance over a wider dynamic range of output drive voltages.

In another example, the operational frequency of the transducer is swept at a given drive voltage while monitoring any of the various operating parameters of the transducer. The magnitude of the operational set point value of the operating parameter is determined at a frequency intermediate the series and parallel resonant frequencies. The transducer can then be operated at a second drive voltage and at the intermediate frequency and the magnitude of the operational set point value of the operating parameter determined at the second drive voltage. Using regression analysis, the magnitude of the operational set point value of the operating parameter can be determined as a function of drive voltage, and the transducer can be operated at any desired drive voltage and the operational set point value can be maintained by varying the frequency.

This description is given for purposes of illustration and explanation. It will be apparent to those skilled in the relevant art that changes and modifications may be made to the invention described above without departing from its scope or spirit.

We claim:

1. A method of tuning an ultrasonic device comprising the steps of:

a) providing alternating current within a frequency range to the ultrasonic device;

b) determining an admittance of the ultrasonic device at a plurality of specific frequencies within the frequency range;

c) determining a series resonant frequency of the ultrasonic device;

d) determining a parallel resonant frequency of the ultrasonic device;

f) determining an admittance value at a frequency intermediate the series resonant frequency and the parallel resonant frequency; and g) operating the ultrasonic device at the admittance value by varying an operational frequency of the ultrasonic device.

2. The method of claim 1 wherein the ultrasonic device comprises a piezoelectric transducer.

3. The method of claim 1 wherein the frequency range is between 20 kilohertz and 100 kilohertz.

4. The method of claim 1 wherein the frequency intermediate the series resonant frequency and the parallel resonant frequency is the average of the series resonant frequency and the parallel resonant frequency.

5. The method of claim 1 wherein the frequency intermediate the series resonant frequency and the parallel resonant frequency is calculated using the formula $f_o = (f_s * \alpha) + (f_p * (1-\alpha))$, where $0 < \alpha < 1$.

6. A method of tuning a piezoelectric transducer comprising the steps of:

a) providing alternating current within a frequency range of 20 kilohertz to 100 kilohertz to the piezoelectric transducer;

b) determining an admittance of the piezoelectric transducer at a plurality of specific frequencies within the frequency range;

c) determining a series resonant frequency of the piezoelectric transducer;

d) determining a parallel resonant frequency of the piezoelectric transducer;

f) determining a constant admittance value at a frequency intermediate the series resonant frequency and the parallel resonant frequency; and g) operating the piezoelectric transducer at the constant admittance value by varying an operational frequency of the ultrasonic device.

7. The method of claim 6 wherein the frequency intermediate the series resonant frequency and the parallel resonant frequency is the average of the series resonant frequency and the parallel resonant frequency.

8. The method of claim 6 wherein the frequency intermediate the series resonant frequency and the parallel resonant frequency is calculated using the formula $f_o = (f_s * \alpha) + (f_p * (1-\alpha))$, where $0 < \alpha < 1$.

9. A method of tuning an ultrasonic device operating within a frequency range, comprising the steps of:

a) applying a first drive voltage to the ultrasonic device;

b) determining a first series resonant frequency and a first parallel resonant frequency within the frequency range at the first drive voltage;

c) determining a magnitude of at least one operational set point parameter at both the first series resonant frequency and the first parallel resonant frequency at the first drive voltage;

d) applying a second drive voltage to the ultrasonic device;

e) determining a second series resonant frequency and a second parallel resonant frequency within the frequency range at the second drive voltage;

f) determining the magnitude of at least one operational set point parameter at both the second series resonant frequency and the second parallel resonant frequency at the second drive voltage;

g) determining the variance in the operational set point parameter magnitude as a function of drive voltage and frequency; and h) operating the ultrasonic device at a desired operational set point parameter value by applying a desired drive voltage and varying the frequency within the frequency range.

10. The method of claim 9 wherein the ultrasonic device comprises a piezoelectric transducer.

11. The method of claim 9 wherein the frequency range is between 20 kilohertz and 100 kilohertz.

12. A method of tuning an ultrasonic device comprising the steps of:

a) applying a first drive voltage to the ultrasonic device;

b) determining a series resonant frequency and a parallel resonant frequency within the frequency range at the first drive voltage;

c) determining a magnitude of at least one operational set point parameter at a selected frequency at the first drive voltage;

d) applying a second drive voltage to the ultrasonic device;

e) determining a magnitude of at least one operational set point parameter at a selected frequency at the second drive voltage;

f) determining the variance in the operational set point parameter magnitude as a function of drive voltage; and g) operating the ultrasonic device at a desired operational set point parameter value by applying a desired drive voltage and varying the frequency within the frequency range.

13. The method of claim 12 wherein the selected frequency is calculated using the formula $f_o = (f_s * \alpha) + (f_p * (1-\alpha))$, where $0 < \alpha < 1$.

14. The method of claim 12 wherein the ultrasonic device comprises a piezoelectric transducer.

15. The method of claim 12 wherein the frequency range is between 20 kilohertz and 100 kilohertz.

* * * * *